(12) United States Patent
Neya et al.

(10) Patent No.: US 11,325,840 B1
(45) Date of Patent: May 10, 2022

(54) ZINC OXIDE POWDER, DISPERSION, PAINT, AND COSMETIC

(71) Applicant: SUMITOMO OSAKA CEMENT CO., LTD., Tokyo (JP)

(72) Inventors: Tadashi Neya, Tokyo (JP); Masahiro Nobe, Tokyo (JP); Syunsuke Suma, Tokyo (JP)

(73) Assignee: SUMITOMO OSAKA CEMENT CO., LTD., Tokyo (JP)

( * ) Notice: Subject to any disclaimer, the term of this patent is extended or adjusted under 35 U.S.C. 154(b) by 0 days.

(21) Appl. No.: 17/393,228

(22) Filed: Aug. 3, 2021

(30) Foreign Application Priority Data

Nov. 30, 2020 (JP) .............................. JP2020-198864

(51) Int. Cl.
| | |
|---|---|
| *C01G 9/02* | (2006.01) |
| *A61K 8/27* | (2006.01) |
| *B82Y 40/00* | (2011.01) |
| *C09D 1/00* | (2006.01) |

(52) U.S. Cl.
CPC .................. *C01G 9/02* (2013.01); *A61K 8/27* (2013.01); *A61K 2800/10* (2013.01); *B82Y 40/00* (2013.01); *C01P 2004/64* (2013.01); *C01P 2006/12* (2013.01); *C09D 1/00* (2013.01)

(58) Field of Classification Search
None
See application file for complete search history.

(56) References Cited

U.S. PATENT DOCUMENTS

2014/0044971 A1  2/2014  Sueda et al.

FOREIGN PATENT DOCUMENTS

| | | |
|---|---|---|
| JP | 11-181329 A | 7/1999 |
| JP | 2019-099510 A | 6/2019 |
| WO | 2012/147888 A1 | 11/2012 |

*Primary Examiner* — Colin W. Slifka
(74) *Attorney, Agent, or Firm* — Merchant & Gould P.C.

(57) ABSTRACT

A zinc oxide powder in which a BET specific surface area of the powder is 8 $m^2/g$ or more and 65 $m^2/g$ or less, an apparent specific volume measured by a loose packing method of the powder is 1.0 mL/g or more and 7.5 mL/g or less, and a value indicated by (the apparent specific volume measured by the loose packing method/an apparent specific volume measured by a tapping method), which is obtained by dividing the apparent specific volume (mL/g) measured by the loose packing method by the apparent specific volume (mL/g) measured by the tapping method of the powder, is 1.50 or more and 2.50 or less.

14 Claims, No Drawings

ZINC OXIDE POWDER, DISPERSION, PAINT, AND COSMETIC

FIELD OF THE INVENTION

The present invention relates to a zinc oxide powder, a dispersion, a paint, and a cosmetic.

This application claims the benefit of Japanese Patent Application No. 2020-198864 filed on Nov. 30, 2020, the disclosure of which is herein incorporated by reference in its entire.

BACKGROUND OF THE INVENTION

Zinc oxide powders have an ultraviolet-shielding function, a gas transmission-suppressing function, and the like and are also highly transparent. Therefore, zinc oxide powders are used for applications requiring an ultraviolet-shielding property and transparency such as ultraviolet-shielding films, ultraviolet-shielding glass, gas barrier films, and cosmetics.

As one of methods for obtaining transparency, reduction of the primary particle sizes of zinc oxide particles to a nano-size level is exemplified. Regarding a method for manufacturing fine zinc oxide particles, a variety of methods such as a thermal decomposition method and a gas phase method are being studied.

For example, Patent Document 1 describes as follows. Fine zinc oxide particles are fine particles, and thus the particles are likely to agglomerate, the independence of the particles becomes poor, and the oil absorption amount becomes high. In the case of blending the fine zinc oxide particles having a high oil absorption amount into a cosmetic, the fine zinc oxide particles absorb a large amount of an oil component that is contained in the cosmetic, whereby the viscosity of the cosmetic becomes high. Furthermore, when the fine zinc oxide particles agglomerate and become poor in dispersibility, the transparency deteriorates. Therefore, in the case of being used in a state of being blended into a cosmetic (in the case of being applied to skin), the agglomerated fine zinc oxide particles also have a disadvantage of becoming unnaturally white. For fine zinc oxide particles, there has been a demand for decreasing the oil absorption amount or the powder volume while enhancing the ultraviolet-shielding property.

Patent Document 1 describes that, in order to solve the problem of the viscosity or transparency caused by the agglomeration, zinc oxide particles in which the primary particle size is less than 0.1 μm, the aspect ratio is less than 2.5, and the oil absorption amount/BET specific surface area is 1.5 mL/100 $m^2$ or less are provided.

Patent Document 2 describes an organic-inorganic composite pigment in which a specific surface treatment is performed on a highly oil-absorbing inorganic pigment in order to clarify the color of the appearance at the time of being blended into a cosmetic and to improve durability.

Patent Document 3 describes a cosmetic containing a liquid-form perfluoroorganic organic compound, a cyclic silicone or a chain-like silicone having a specific volatilization rate, and an oil-absorbing powder having a high oil absorption amount capable of absorbing squalane that weighs 1.5 times or more the weight of the oil-absorbing powder. This cosmetic has a refreshing feel during use and is capable of preventing temporal makeup deterioration such as shiny skin.

PRIOR ART LITERATURE

Patent Documents

Patent Document 1: Japanese Translation of PCT International Application, Publication No. 2012/147888
Patent Document 2: Japanese Unexamined Patent Application, First Publication No. H11-181329
Patent Document 3: Japanese Unexamined Patent Application, First Publication No. 2019-099510

SUMMARY OF THE INVENTION

Inorganic powders having a high oil absorption amount had an advantage of capable of imparting a feel during use to cosmetics or preventing the problem of temporal makeup deterioration such as shiny skin.

However, inorganic powders having a high oil absorption amount of the related art had a disadvantage of temporally increasing the viscosity of cosmetics or the like in the case of being blended into the cosmetics or the like.

There has been a demand for developing an excellent zinc oxide powder solving the above-described disadvantage while having the above-described advantage.

The present invention has been made in view of the above-described circumstances, and an object of the present invention is to provide a zinc oxide powder capable of suppressing a temporal increase in the viscosity in the case of being blended into cosmetics or the like and having a high oil absorption amount to a favorable degree and a dispersion, a paint, and a cosmetic that each contain the zinc oxide powder. In addition, another object of the present invention is to impart the same degree of transparency or the like as in the related art to the zinc oxide powder.

Means for Solving the Problems

That is, in a zinc oxide powder of a first aspect of the present invention, a BET specific surface area of the powder is 8 $m^2$/g or more and 65 $m^2$/g or less, an apparent specific volume measured by a loose packing method of the powder is 1.0 mL/g or more and 7.5 mL/g or less, and a value indicated by (the apparent specific volume measured by the loose packing method/an apparent specific volume measured by a tapping method), which is obtained by dividing the apparent specific volume (mL/g) measured by the loose packing method by the apparent specific volume (mL/g) measured by the tapping method of the powder, is 1.50 or more and 2.50 or less.

The zinc oxide powder of the first aspect of the present invention may be further surface-treated.

A zinc oxide powder that is not surface-treated and a surface-treated zinc oxide powder that has been surface-treated may be used in combination.

A dispersion of a second aspect of the present invention contains the zinc oxide powder of the first aspect of the present invention and a dispersion medium.

A cosmetic of a third aspect of the present invention contains the zinc oxide powder of the first aspect of the present invention, a resin, and a dispersion medium.

A cosmetic of a fourth aspect of the present invention contains at least one selected from the group consisting of the zinc oxide powder of the first aspect of the present invention and the dispersion of the second aspect of the present invention.

A surface-treated zinc oxide powder of a fifth aspect of the present invention is a surface-treated zinc oxide powder in which the zinc oxide powder of the first aspect of the present invention is surface-treated with at least one of an inorganic component and an organic component.

Effects of the Invention

According to the zinc oxide powder of the present invention, since the BET specific surface area of the powder is 8 $m^2/g$ or more and 65 $m^2/g$ or less, the apparent specific volume measured by the loose packing method of the powder is 1.0 mL/g or more and 7.5 mL/g or less, and the value indicated by (the apparent specific volume measured by the loose packing method/the apparent specific volume measured by the tapping method), which is obtained by dividing the apparent specific volume (mL/g) measured by the loose packing method by the apparent specific volume (mL/g) measured by the tapping method of the powder, is 1.50 or more and 2.50 or less, the zinc oxide powder is capable of suppressing a temporal increase in the viscosity in the case of being blended into cosmetics or the like.

In addition, the zinc oxide powder of the present invention is capable of maintaining an appropriate oil absorption amount and is capable of maintaining excellent transparency or the like in the case of being blended into dispersions or the like. In addition, even in a case where the zinc oxide powder is surface-treated, it is possible to provide the above-described excellent effects.

According to the dispersion of the present invention, since either or both of the zinc oxide powder of the present invention and the surface-treated zinc oxide powder of the present invention and a dispersion medium are contained, it is possible to suppress a temporal increase in the viscosity of the dispersion.

According to the paint of the present invention, since either or both of the zinc oxide powder of the present invention and the surface-treated zinc oxide powder of the present invention, a resin, and a dispersion medium are contained, it is possible to suppress a temporal increase in the viscosity of the paint.

According to the cosmetic of the present invention, since at least one selected from the group consisting of the zinc oxide powder of the present invention and the dispersion of the present invention is contained, it is possible to suppress a temporal increase in the viscosity of the cosmetic.

DETAILED DESCRIPTION OF THE INVENTION

An embodiment that is a preferred example of a zinc oxide powder, a dispersion, a paint, and a cosmetic of the present invention will be described.

The present embodiment is simply a specific description for better understanding of the gist of the present invention and does not limit the present invention unless particularly specified. Omission, addition, substitution, and other modifications are possible within the scope of the gist of the present invention.

Zinc Oxide Powder

In a zinc oxide powder of the present embodiment, the BET specific surface area of the powder is 8 $m^2/g$ or more and 65 $m^2/g$ or less, the apparent specific volume measured by a loose packing method of the powder is 1.0 mL/g or more and 7.5 mL/g or less, and a value indicated by (the apparent specific volume measured by the loose packing method/the apparent specific volume measured by a tapping method), which is obtained by dividing the apparent specific volume (mL/g) measured by the loose packing method by the apparent specific volume (mL/g) measured by the tapping method of the powder, is 1.50 or more and 2.50 or less. In the present specification, the apparent specific volume measured by the loose packing method can also be differently referred to as the loosely packed volume. In addition, the apparent specific volume measured by the tapping method can also be differently referred to as the tapped volume.

The content of zinc oxide in the zinc oxide powder of the embodiment is preferably 99.5% by mass or more, more preferably 99.7% by mass or more, and still more preferably 100% by mass. The zinc oxide powder may consist of zinc oxide, but may contain an extremely small amount of impurities to an extent that the effect is not affected. In addition, the zinc oxide powder of the embodiment also preferably consists of zinc oxide particles. The content of zinc oxide in the zinc oxide powder of the present embodiment refers to a value measured by the following method. This measurement method is a measurement method according to "Determination of Zinc Oxide" described in the Japanese Standards of Quasi-drug Ingredients 2006 (Supplement to the Japanese standards of quasi-drug ingredients).

The zinc oxide powder is put into a muffle furnace and ignited at 500° C. until the mass becomes constant (a state where the mass does not change is formed). After that, the zinc oxide powder is naturally cooled to room temperature in a glass desiccator containing silica gel. The naturally cooled zinc oxide powder is accurately weighed to 1.5 g, water (50 mL) and dilute hydrochloric acid (20 mL) are added thereto, and the mixture is heated to dissolve the zinc oxide powder. In a case where an unwanted substance remains, three droplets of nitric acid are added to the solution to fully dissolve the unwanted substance. This solution is cooled to room temperature, and the total amount is adjusted to 250 mL by adding water. An acetic acid-ammonium acetate buffer solution having a pH adjusted to 5.0 (10 mL) is added to this solution (25 mL), and the pH is adjusted to 5 to 5.5 by adding diluted ammonia water. After that, the amount is adjusted to 250 mL by adding water, a xylenol orange reagent (0.5 mL) is added to the solution as an indicator, and the solution is titrated with a 0.05 mol/L disodium edetate solution until the solution turns yellow. Since 1 mL of the 0.05 mol/L disodium edetate solution is equivalent to 4.069 mg of zinc oxide, it is possible to determine the content of zinc oxide in the zinc oxide powder from the amount of the 0.05 mol/L disodium edetate solution required for the titration. In the present measurement method, in a case where a value of more than 100% by mass is calculated, the content of zinc oxide is regarded as 100% by mass.

Method for Measuring Each Characteristic of Zinc Oxide Powder or Surface-Treated Zinc Oxide Powder The BET specific surface area in the zinc oxide powder of the present embodiment may refer to a value measured by the BET method using a specific surface area-measuring device, for example, as a specific example, a full automatic specific surface area analyzer (trade name: Macsorb HM Model-1201 manufactured by Mountech Co., Ltd.).

The apparent specific volume (mL/g) measured by the loose packing method in the zinc oxide powder of the present embodiment refers to a value measured in accordance with JIS K 5101-12-1 "Test methods for pigments—Part 12: Apparent density or apparent specific volume—Section 1: Loose packing method". For the apparent specific volume measured by the loose packing method, tapping is performed 50 times.

The apparent specific volume (mL/g) measured by the tapping method in the zinc oxide powder of the present embodiment can be measured using a bulk density-measuring device, for example, as a specific example, a closely packed bulk density-measuring device (trade name: TVP-1 type, manufactured by Tsutsui Scientific Instruments Co., Ltd.). A specific measurement method will be described.

The mass (A) of a 150 mL graduated cylinder (inner diameter: 31 mm, manufactured by Tsutsui Scientific Instruments Co., Ltd.) is measured with an electronic balance. Zinc oxide powder (100 mL or more) is placed on a sieve having a mesh diameter of 500 μm. Next, the zinc oxide powder is wiped with a brush, and the zinc oxide powder is sifted. The zinc oxide powder that has passed through the sieve (approximately 100 mL) is put into the 150 mL graduated cylinder. The mass (B) of this graduated cylinder is measured with the electronic balance. This graduated cylinder is fixed to the closely packed bulk density-measuring device. The graduated cylinder is covered with a black rubber stopper so as to prevent the powder from scattering during tapping. The volume (V) of the zinc oxide powder at the time of performing tapping 50 times with the closely packed bulk density-measuring device is read from the graduated cylinder. Next, the apparent specific volume is calculated by V/(B−A). It is possible to set the tapping width to 20 mm and the tapping speed to 30 times/minute. As described above, the tapping method is a method in which a container containing powder is tapped a plurality of times to tamp the powder in the container and measurement is performed.

The dry particle diameter D98 in the zinc oxide powder of the present embodiment may refer to the value of the particle diameter at a cumulative volume percentage of 98% in the case of measuring the volume particle size distribution of the zinc oxide powder in a dry manner using a laser diffraction-type particle size distribution-measuring device, for example, as a specific example, a laser diffraction-type particle size distribution-measuring device (Model No.: Mastersizer 3000, manufactured by Malvern Panalytical Ltd.). Hereinafter, there will be cases where the dry particle diameter D98 is abbreviated as "D98".

The crystallite diameter in the zinc oxide powder of the present embodiment may refer to the Scherrer diameter calculated from the Scherrer equation using the full width at half maximum and diffraction angle (2θ) of a diffraction peak of a (101) plane in a powder X-ray diffraction pattern measured with an X-ray diffraction apparatus, for example, as a specific example, an X-ray diffraction apparatus (trade name: AERIS, manufactured by Malvern Panalytical Ltd.).

Regarding the measurement conditions for the X-ray diffraction of the powder using the above-described apparatus, CuKα radiation is used as the radiation source, the output is set to 40 kV and 15 mA. In addition, measurement data that are obtained by X-ray diffraction measurement can be analyzed using data processing software AERIS (manufactured by Malvern Panalytical Ltd.), which makes it possible for the Scherrer diameter to be calculated.

The oil absorption amount of the zinc oxide powder of the present embodiment refers to a value measured in accordance with JIS K5101-13-1 (Test methods for pigments—Part 13: Oil absorption—Section 1: Refined linseed oil method).

BET Specific Surface Area

The BET specific surface area in the zinc oxide powder of the present embodiment is 8 m$^2$/g or more and 65 m$^2$/g or less, preferably 15 m$^2$/g or more and 60 m$^2$/g or less, more preferably 20 m$^2$/g or more and 50 m$^2$/g or less, and still more preferably 25 m$^2$/g or more and 45 m$^2$/g or less.

When the BET specific surface area of the zinc oxide powder is adjusted to the above-described range, it is possible to enhance the transparency of dispersions, paints, cosmetics, and the like that contain this zinc oxide powder and also to maintain the viscosity within a preferable range.

When the BET specific surface area is less than 8 m$^2$/g, the transparency of dispersions tends to deteriorate in a case where the zinc oxide powder is contained in a high concentration, which is not preferable. On the other hand, when the BET specific surface area exceeds 65 m$^2$/g, in a case where the zinc oxide powder is contained in a high concentration, the viscosity of dispersions is likely to increase, and there is a tendency that it becomes difficult to obtain uniform and highly fluid dispersions, which is not preferable.

The method for adjusting the BET specific surface area of the zinc oxide powder to the above-described range is not particularly limited, and an exemplary example is a method in which the average primary particle size converted from the BET specific surface area (BET-converted particle diameter) is adjusted to 15 nm or more and 110 nm or less. Ordinarily, as the primary particle size becomes larger, the BET specific surface area becomes smaller, and, as the primary particle size becomes smaller, the BET specific surface area becomes larger.

In addition, the BET specific surface area of the zinc oxide powder can be adjusted by adjusting the particle shapes or by providing micropores to the particles.

The zinc oxide powder of the present embodiment is, usually, formed of secondary particles, but may contain primary particles. In a case where the zinc oxide powder contains primary particles, the fractions of zinc oxide secondary particles and zinc oxide primary particles in the zinc oxide powder can be arbitrarily selected. For example, the fraction of the secondary particles may be 70% by mass or more, 80% by mass or more, 90% by mass or more, 95% by mass or more, 98% by mass or more, or 100% by mass.

Apparent Specific Volume Measured by Loose Packing Method

The apparent specific volume measured by the loose packing method in the zinc oxide powder of the present embodiment is 1.0 mL/g or more and 7.5 mL/g or less, preferably 3.0 mL/g or more and 7.5 mL/g or less, more preferably 4.0 mL/g or more and 7.5 mL/g or less, and still more preferably 5.0 mL/g or more and 7.5 mL/g or less.

When the apparent specific volume measured by the loose packing method of the zinc oxide powder is adjusted to the above-described range, it is possible to suppress a temporal increase in the viscosity of dispersions at the time of mixing the zinc oxide powder into a dispersion medium. That is, the viscosity of the dispersion is unlikely to increase even when time has passed.

When the apparent specific volume measured by the loose packing method is less than 1.0 mL/g, there is a tendency for the transparency of dispersions containing the zinc oxide powder to deteriorate, which is not preferable. On the other hand, when the apparent specific volume measured by the loose packing method exceeds 7.5 mL/g, there is a tendency for the viscosity of dispersions containing the zinc oxide powder to temporally increase, which is not preferable. As an example of a cause for increasing the apparent specific volume measured by the loose packing method, for example, a small particle size is exemplified, but the cause is not limited thereto.

The method for controlling the apparent specific volume measured by the loose packing method of the zinc oxide powder to be within the above-described range is not particularly limited. For example, in the case of producing the zinc oxide powder using a thermal decomposition method as described in Japanese Laid-open Patent Publication No. 60-255620, it is possible to control the apparent specific volume measured by the loose packing method of the zinc oxide powder to be within the above-described range by adjusting the apparent specific volume measured by the loose packing method of zinc oxalate, zinc hydroxide, zinc carbonate, basic zinc carbonate, or the like, which is a raw material, or by adjusting the thermal decomposition temperature.

For example, in the case of producing zinc oxide using a gas phase method as described in Japanese Laid-open Patent Publication No. 63-288914, it is possible to control the apparent specific volume measured by the loose packing method of the zinc oxide powder to be within the above-described range by appropriately adjusting temperatures in the production process.

(Apparent Specific Volume Measured by Loose Packing Method/Apparent Specific Volume Measured by Tapping Method)

There have been a number of unclear points regarding the apparent specific volume characteristic of the powder and an effect thereof. However, as a result of paying attention to the characteristics of the apparent specific volume measured by the loose packing method and the apparent specific volume measured by tapping method, it has become possible to provide an excellent zinc oxide powder in which an increase in the viscosity is prevented while maintaining the oil-absorbing property.

In the zinc oxide powder of the present embodiment, a value obtained by dividing the apparent specific volume (mL/g) measured by the loose packing method by the apparent specific volume (mL/g) measured by the tapping method (the apparent specific volume measured by the loose packing method/the apparent specific volume measured by the tapping method) is 1.50 or more and 2.50 or less. "The apparent specific volume measured by the loose packing method/the apparent specific volume measured by the tapping method" is preferably 1.55 or more and 2.30 or less and more preferably 1.60 or more and 2.00 or less.

When "the apparent specific volume measured by the loose packing method/the apparent specific volume measured by the tapping method" is 1.50 or more and 2.50 or less, it is possible to suppress a temporal increase in the viscosity of dispersions containing the zinc oxide powder. In a case where "the apparent specific volume measured by the loose packing method/the apparent specific volume measured by the tapping method" is outside the above-described range, it is difficult to suppress a temporal increase in the viscosity.

The mechanism that makes it possible to suppress a temporal increase in the viscosity of dispersions containing the zinc oxide powder by controlling "the apparent specific volume measured by the loose packing method/the apparent specific volume measured by the tapping method" to be within the above-described range is not clear. However, it is assumed as follows.

The apparent specific volume measured by the loose packing method is the value of the volume of the powder per unit mass measured in a state where an air is contained among the particles in the powder. In contrast, the apparent specific volume measured by the tapping method is a value of the volume of the powder per unit mass measured in a state where some of the air among the particles of the powder has been removed by tapping. Therefore, the apparent specific volume measured by the loose packing method of the powder is usually larger than the apparent specific volume measured by the tapping method. In addition, ordinarily, as the particles of the powder become smaller, the amount of the air among the particles becomes larger, and the apparent specific volume measured by the loose packing method becomes larger.

In a case where the zinc oxide particles that configure the zinc oxide powder are coarse particles that are dense inside, it becomes difficult to contain an excess air among the particles. Since it is difficult for such particles to contain an air among the particles even during the measurement of the apparent specific volume measured by the loose packing method, the value of the apparent specific volume measured by the loose packing method becomes small, the apparent specific volume measured by the tapping method remains almost unchanged, and the value of "the apparent specific volume measured by the loose packing method/the apparent specific volume measured by the tapping method" becomes close to one. Zinc oxide powders containing coarse zinc oxide particles have large agglomerated particle diameters and are thus poor in transparency.

In addition, in the case of particles in which a number of pores are generated in the zinc oxide particles, agglomerated particles in which a steric barrier (fusion of agglomerated particles) in which a branched structure or the like attributed to the fusion between the zinc oxide particles is significantly formed is generated, or the like, the value of the apparent specific volume measured by the loose packing method becomes larger than the value of the coarse zinc oxide particles. For such particles, the air in the particles or among the particles is not removed in the method for measuring the apparent specific volume measured by the tapping method, in which vibration is applied by tapping, and the apparent specific volume of the powder remains almost unchanged. That is, the large value of the apparent specific volume measured by the tapping method remains unchanged, and the value of "the apparent specific volume measured by the loose packing method/the apparent specific volume measured by the tapping method" becomes close to one. On the other hand, in a case where particles having such a structure or agglomerated particles are used, the structure of the zinc oxide particles collapses due to an applied force or the like at the time of dispersing the zinc oxide powder or the surface-treated zinc oxide powder in a solvent. As a result, a fine powder is generated or the active surfaces of the zinc oxide particles are exposed, and the viscosity of dispersions increases.

Therefore, in order to increase the transparency and suppress an increase in the viscosity of dispersions, "the apparent specific volume measured by the loose packing method/the apparent specific volume measured by the tapping method" needs to be 1.50 or more.

On the other hand, "the apparent specific volume measured by the loose packing method/the apparent specific volume measured by the tapping method" exceeding 2.50 means that a number of fine zinc oxide particles are included among the zinc oxide particles that configure the zinc oxide powder. When incorporated into the zinc oxide powder, zinc oxide particles having extremely fine particle diameters act as a cause of re-agglomeration of the zinc oxide particles in dispersions even after being dispersed in the dispersions. Therefore, due to such a temporal change, there is a tendency that the viscosity of the dispersions increases and the transparency of the dispersions also deteriorates. Therefore, "the apparent specific volume measured by the loose packing method/the apparent specific volume measured by the tapping method" needs to be 2.50 or less.

Controlling "the apparent specific volume measured by the loose packing method/the apparent specific volume measured by the tapping method" makes it possible to appropriately adjust the structure, size, or the like of the zinc oxide particles and makes the transparency and dispersion stability of the dispersion maintained. That is, "the apparent specific volume measured by the loose packing method/the apparent specific volume measured by the tapping method" in the zinc oxide powder of the present embodiment enables the macroscopic understanding of the microscopic behaviors or structure of each zinc oxide particle and enables the obtainment of an excellent zinc oxide powder containing no particles having a unpreferable structure. As described above, "the apparent specific volume measured by the loose packing method/the apparent specific volume measured by the tapping method" is an excellent parameter.

Therefore, it is possible to obtain an excellent zinc oxide powder and an excellent dispersion in which a temporal increase in the viscosity is suppressed and the dispersion stability is excellent by measuring "the apparent specific volume measured by the loose packing method/the apparent specific volume measured by the tapping method" and controlling the sizes of the zinc oxide particles that configure the zinc oxide powder or the structure of the zinc oxide particles such that the apparent specific volume measured by the loose packing method/the apparent specific volume measured by the tapping method becomes 1.50 or more and 2.50 or less. The manufacturing conditions or materials are preferably appropriately selected such that "the apparent specific volume measured by the loose packing method/the apparent specific volume measured by the tapping method" is included in the preferable range.

D98/BET-Converted Particle Diameter

In the zinc oxide powder of the present embodiment, a value obtained by dividing the dry particle diameter D98 (μm) by the BET-converted particle diameter (nm) (D98 (μm)/BET-converted particle diameter (nm)) is preferably 0.01 or more and 5.00 or less, more preferably 0.01 or more and 4.0 or less, and still more preferably 0.01 or more and 3.0 or less. The value may be 0.01 to 3.5, 0.05 to 2.0, 0.10 to 1.00, 0.15 to 0.80, 0.20 to 0.60, or the like as necessary. When "D98/converted diameter" is within the above-described range, it is possible to suppress the texture of rough surface of the zinc oxide powder, which is preferable.

The surface-treated zinc oxide powder obtained by surface-treating the zinc oxide powder of the present embodiment, which will be described below, may have (D98 (μm)/BET-converted particle diameter (nm)) in the above-described range.

BET-Converted Particle Diameter

In the present specification, the "BET-converted particle diameter (nm)" refers to a particle diameter converted from the BET specific surface area (m²/g) of the zinc oxide powder using General Formula (1) shown below.

$$\text{BET-converted particle diameter (nm)}=6000/(\text{BET specific surface area (m}^2/\text{g)} \times \rho \text{ (g/cm}^3)) \quad (1)$$

In Formula (1), $\rho$ is the density of zinc oxide, and, in the present embodiment, $\rho$ of 5.61 g/cm³ is used. The BET-converted particle diameter (nm) of the zinc oxide powder can be arbitrarily selected. For example, the particle diameter may be 15 to 110 nm or 15 to 100 nm. The particle diameter may be 15 to 80 nm, 20 to 50 nm, 25 to 45 nm, 30 to 35 nm, or the like as necessary.

Method for Manufacturing Zinc Oxide Powder and Method for Adjusting Apparent Specific Volume A method for manufacturing the zinc oxide powder of the present embodiment is not particularly limited. For example, as the method for manufacturing the zinc oxide powder, there is a method in which, as described in Japanese Laid-open Patent Publication No. S60-255620, zinc oxalate, zinc hydroxide, zinc carbonate, basic zinc carbonate, or the like, which serves as a raw material, is produced by a thermal decomposition method. In addition, for example, there is a method in which zinc oxide powder is produced by a gas phase method in which metallic zinc vapor is oxidatively combusted as described in Japanese Laid-open Patent Publication No. S63-288014.

In order to produce the zinc oxide powder of the present embodiment, for example, a method in which a material that increases the apparent specific volume measured by the loose packing method is added or an apparatus capable of increasing the apparent specific volume measured by the loose packing method is used at the time of manufacturing the zinc oxide powder is exemplified. When the apparent specific volume measured by the loose packing method is set to be large, an effect of enhancing transparency can be obtained. Regarding the control over the apparent specific volume of the powder, a desired value can be obtained by combining a method described below, a method that has been used in the related art, and the like. Here, an excellent effect that can be obtained by controlling the value of the apparent specific volume of the powder to be within a predetermined range has not yet been known and predicted.

In order to increase the apparent specific volume measured by the loose packing method of the zinc oxide powder, for example, in the case of using a thermal decomposition method, a method in which a foaming agent is mixed into a raw material for producing the zinc oxide powder in a small amount that is arbitrarily selected, for example, approximately 1% by mass is exemplified. As the foaming agent, it is possible to preferably use, for example, an inorganic foaming agent such as ammonium carbonate, ammonium hydrogen carbonate, ammonium nitrite, sodium boron hydride, calcium azide, sodium bicarbonate, ammonium bicarbonate, ammonium carbonate, ammonium nitrite, neutral magnesium carbonate, ferrous oxalate, ammonium persulfate, or sodium boron hydride or an organic foaming agent such as an azo compound such as azobisisobutyronitrile, a hydrazine compound such as diphenylsulfone-3,3'-disulfohydrazine, a semicarbazide compound, a triazole compound, or an N-nitroso compound.

Examples of an example of an apparatus for increasing the apparent specific volume measured by the loose packing method of the zinc oxide powder include a fluidized-bed calcinating furnace and the like capable of calcinating while feeding an air.

The apparent specific volume measured by the loose packing method and "the apparent specific volume measured by the loose packing method/the apparent specific volume measured by the tapping method" can be adjusted to desired ranges by adjusting the amount of the foaming agent or the calcinating temperature.

Examples of the method for manufacturing the zinc oxide powder of the present embodiment include a method in which ammonium carbonate (1% by mass), which is a foaming agent, is added to zinc carbonate having an apparent specific volume measured by the loose packing method of 1.0 mL/g to 7.5 mL/g and thermally decomposed at 300° C. to 700° C., preferably, 400° C. to 600° C. in a fluidized-bed calcinating furnace.

The method for adjusting D98 is not particularly limited, and D98 can be adjusted by, for example, performing a cracking treatment on the zinc oxide powder under preferable conditions. The cracking treatment is not particularly limited as long as the cracking treatment is a method in which individual particles (agglomerated particles and/or an aggregate of particles) in the zinc oxide powder can be cracked so as to obtain a desired D98. As an example of the cracking treatment, a method in which individual particles are cracked using a crusher is exemplified. Examples of the crusher include a roller mill, a hammer mill, a cage mill, a pin mill, a disintegrator, a pulverizer, an atomizer, a turbo mill, a super micron mill, a fine micron mill, a tumbling ball mill, a vibration ball mill, a planet mill, a tower mill, an attritor, a basket mill, a CF mill, a sand grinder, a dyno mill, an ultra-visco mill, a coball mill, a swirling-type jet mill, a fluidized-bed jet mill, a nanomizer, a shear mill, a colloid mill, and the like.

The method for adjusting D98 as described above may be performed after the surface treatment of the zinc oxide powder of the present embodiment as described below. That is, the cracking treatment may be performed on the surface-treated zinc oxide powder under preferable conditions so as to obtain a desired D98.

Crystallite Diameter

The crystallite diameter of the zinc oxide powder of the present embodiment is preferably 15 nm or more and 26 nm or less. The crystallite diameter may be 15 nm or more and 20 nm or less, 15 nm or more and 18 nm or less, 19 nm or more and 23 nm or less, or the like as necessary.

Crystallite Diameter (Nm)/BET-Converted Particle Diameter (nm)

In the zinc oxide powder of the present embodiment, a value obtained by dividing the crystallite diameter (nm) by the BET-converted particle diameter (nm) obtained from the BET specific surface area is preferably 0.1 or more and 1.0 or less, more preferably 0.4 or more and 1.0 or less, still more preferably 0.5 or more and 1.0 or less, and far still more preferably 0.6 or more and 1.0 or less. The value may be 0.2 or more and 0.9 or less, 0.3 or more and 0.8 or less, or the like as necessary.

The zinc oxide powder having a BET specific surface area of 8 $m^2/g$ or more and 65 $m^2/g$ or less and a crystallite diameter of 15 nm or more and 26 nm or less has crystallinity favorable enough to obtain high transparency and a high ultraviolet-shielding property.

In order to improve the crystallinity of the zinc oxide powder, there is a need to increase, for example, temperatures in the production process of the zinc oxide powder to an extent that grains do not excessively grow.

Oil Absorption Amount

The zinc oxide powder of the present embodiment may have a preferable oil absorption amount that is arbitrarily selected. For example, the oil absorption amount may be 80 to 150 mL/100 g or 85 to 145 mL/100 g. The oil absorption amount may be 90 to 140 mL/100 g, 95 to 135 mL/100 g, 100 to 130 mL/100 g, 110 to 120 mL/100 g, or the like as necessary.

Surface-Treated Zinc Oxide Powder

For the zinc oxide powder of the present embodiment, a surface treatment may be performed on at least some of the surface of the zinc oxide powder with at least one of an inorganic component and an organic component. The zinc oxide powder on which the surface treatment has been performed with at least one of an inorganic component and an organic component as described above will be referred to as surface-treated zinc oxide powder.

The inorganic component and the organic component are appropriately selected depending on the applications of the zinc oxide powder.

In a case where the surface-treated zinc oxide powder of the present embodiment is used for cosmetics, the inorganic component and the organic component are not particularly limited as long as the inorganic component and the organic component are a surface treatment agent that is ordinarily used for cosmetics.

Examples of an example of the inorganic component include silica, alumina, and the like.

Examples of an example of the organic component include at least one component selected from the group consisting of a silane compound, a silicone compound, a fatty acid, a fatty acid soap, a fatty acid ester, and an organic titanate compound.

In addition, as the inorganic component or the organic component, a surfactant may be used.

In a case where the zinc oxide powder is surface-treated with at least one of the inorganic component and the organic component described above, it is possible to suppress the surface activity of the zinc oxide powder or to improve the dispersibility of the zinc oxide powder in dispersion media.

Examples of the silane compound that is used for the surface treatment include an alkylsilane such as methyltrimethoxysilane, ethyltrimethoxysilane, hexyltrimethoxysilane, octyltrimethoxysilane, or octyltriethoxysilane; a fluoroalkylsilane such as trifluoromethylethyltrimethoxysilane or heptadecafluorodecyltrimethoxysilane; and the like. Among these silane compounds, the alkylsilane is preferred, and octyltriethoxysilane is particularly preferred.

These silane compounds may be used singly or two or more silane compounds may be used in combination.

Examples of the silicone compound that is used for the surface treatment include silicone oil such as methyl hydrogen polysiloxane, dimethylpolysiloxane, or methyl phenyl polysiloxane; methicone, dimethicone, hydrogen dimethicone, triethoxysilylethyl polydimethylsiloxyethyl dimethicone, triethoxysilylethyl polydimethylsiloxyethylhexyl dimethicone, (acrylate/tridecyl acrylate/triethoxysilylpropyl methacrylate/dimethicone methacrylate) copolymers, triethoxycaprylylsilane, and the like. These silicone compounds may be used singly or two or more silicone compounds may be used in combination. In addition, as the silicone compound, a copolymer of these silicone compounds may also be used.

Examples of the fatty acid include palmitic acid, isooctadecanoic acid, stearic acid, lauric acid, myristic acid, behenic acid, oleic acid, rosin acid, 12-hydroxystearic acid, and the like.

Examples of the fatty acid soap include aluminum stearate, calcium stearate, aluminum 12-hydroxystearate, and the like.

Examples of the fatty acid ester include dextrin fatty acid esters, cholesterol fatty acid esters, sucrose fatty acid esters, starch fatty acid esters, and the like.

Examples of the organic titanate compound include isopropyl triisostearoyl titanate, isopropyl dimethacryl isostearoyl titanate, isopropyl tri(dodecyl) benzene sulfonyl titanate, neopentyl (diallyl)oxy tri(dioctyl) phosphate titanate, neopentyl (diallyl)oxy trineododecanoyl titanate, and the like.

In a case where the surface-treated zinc oxide powder of the present embodiment is used for industrial applications of ultraviolet-shielding films, gas barrier films, or the like, in addition to the inorganic component or the organic component that is used for cosmetics, an ordinary dispersant that is used to disperse particles such as an anionic dispersant, a cationic dispersant, a nonionic dispersant, a silane coupling agent, or a wetting dispersant can also be appropriately selected and used as the surface treatment agent.

In a case where the above-described surface treatment is performed, it is possible to suppress the surface activity of the zinc oxide powder or to improve the dispersibility of the zinc oxide powder in dispersion media.

In the surface-treated zinc oxide powder of the present embodiment, a value (D98 (µm)/BET-converted particle diameter (nm)) obtained by dividing the dry particle diameter D98 (µm) of the surface-treated zinc oxide powder by the BET-converted particle diameter (nm) of the surface-treated zinc oxide powder is preferably 0.01 or more and 5.0 or less, more preferably 0.01 or more and 4.5 or less, still more preferably 0.01 or more and 4.0 or less, and far still more preferably 0.01 or more and 3.0 or less. The value may be 0.01 or more and 1.0 or less, 0.15 or more and 0.80 or less, or 0.20 or more and 0.60 or less as necessary. The BET-converted particle diameter of the surface-treated zinc oxide powder can be calculated by obtaining the BET specific surface area of the surface-treated zinc oxide powder and applying this value to General Formula (1). When the "D98/BET-converted particle diameter" of the surface-treated zinc oxide powder is within the above-described range, it is possible to suppress the texture of rough surface of the surface-treated zinc oxide powder.

The BET-converted particle diameter (nm) of the surface-treated zinc oxide powder can be arbitrarily selected. For example, the BET-converted particle diameter may be within a range of 15 to 110 nm, may be 15 to 100 nm, and may be 15 to 80 nm, 20 to 50 nm, 25 to 45 nm, 30 to 35 nm, or the like as necessary.

The BET specific surface area of the surface-treated zinc oxide powder can be obtained by the same method as that of the zinc oxide powder.

The method for manufacturing the surface-treated zinc oxide powder of the present embodiment is not particularly limited, and a well-known method may be appropriately performed depending on a component that is used for the surface treatment.

In addition, the "D98/BET-converted particle diameter" of the surface-treated zinc oxide may be adjusted so as to become 0.01 or more and 5 or less by cracking the zinc oxide powder after the surface treatment. The same crusher as described above can be used for the cracking treatment.

The amount of zinc oxide contained in the surface-treated zinc oxide powder of the present embodiment is preferably 80% to 99% by mass and more preferably 82% to 97% by mass.

Examples of an example of a method for the surface treatment include the following method.

The zinc oxide powder of the present invention that is not surface-treated, at least one of the inorganic component and the organic component that is used for the surface treatment, and, as necessary, one or more arbitrarily-selected solvents such as pure water or isopropyl alcohol are mixed together by an arbitrarily-selected method or apparatus. Preferred examples of the solvents include aqueous solvents and the like. The total amount of the inorganic component and/or the organic component that are mixed may be, for example, 1 to 25 parts by mass and is preferably 3 to 22 parts by mass with respect to 100 parts by mass of the zinc oxide particles. The amount of the solvents can be arbitrarily selected. After the mixing, the mixture obtained at an arbitrarily-selected temperature may be dried in order to remove at least one part of the solvent. The temperature for the drying can be arbitrarily selected and is, for example, 50° C. to 200° C. or the like, preferably 60° C. to 150° C., and more preferably 70° C. to 120° C. In addition, a heat treatment may be performed in order to further progress the surface treatment reaction. The temperature for the heat treatment can be arbitrarily selected and is, for example, 200° C. to 800° C. or the like, preferably 200° C. to 700° C., and more preferably 200° C. to 600° C. The obtained dried substance or heat-treated substance (surface-treated zinc oxide powder) may be cracked by an arbitrarily-selected method or apparatus under an arbitrarily-selected condition until, for example, D98 becomes 500 µm or less. The cracked substance may be further dried. The drying temperature can be arbitrarily selected and is, for example, 50° C. to 200° C. or the like, preferably 60° C. to 150° C., and more preferably 70° C. to 120° C. The surface-treated zinc oxide powder of the present embodiment may be controlled such that the value obtained by dividing the dry particle diameter D98 (µm) by the BET-converted particle diameter (nm) becomes 0.01 or more and 5 or less by controlling a manufacturing condition.

Dispersion

A dispersion of the present embodiment contains the zinc oxide powder of the present embodiment and a dispersion medium. Examples of the dispersion of the present embodiment include a paste-form dispersion having a high viscosity.

The content of the zinc oxide powder in the dispersion of the present embodiment is not particularly limited, can be arbitrarily selected, and is, for example, preferably 10% by mass or more and 90% by mass or less, more preferably 20% by mass or more and 85% by mass or less, and still more preferably 30% by mass or more and 80% by mass or less. When the content of the zinc oxide powder in the dispersion is within the above-described range, a preferred characteristic of the zinc oxide powder can be obtained, and it is possible to suppress a temporal increase in the viscosity of the dispersion.

The dispersion medium is appropriately selected depending on the application of the dispersion. Examples of preferred dispersion media will be described below, but the dispersion medium in the present embodiment is not limited thereto. The following dispersion media may be used singly or dispersion media from the following examples may be used in combination.

As examples of an example of the dispersion medium, for example, water, alcohols such as methanol, ethanol, 1-propanol, 2-propanol, 1-butanol, 2-butanol, octanol, and glycerin; esters such as ethyl acetate, butyl acetate, ethyl lactate, propylene glycol monomethyl ether acetate, and g-butyrolactone; and ethers such as diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, and diethylene glycol monoethyl ether are exemplified, and these dispersion media are preferably used. These dispersion media may be used singly or two or more dispersion media may be used in a mixture form.

In addition, as examples of other dispersion media, ketones such as acetone, methyl ethyl ketone, methyl isobutyl ketone, acetyl acetone, and cyclohexanone; aromatic hydrocarbons such as benzene, toluene, xylene, and ethyl benzene; cyclic hydrocarbon such as cyclohexane; amides such as dimethylformamide, N,N-dimethylacetoacetamide, and N-methylpyrrolidone; and chain-like polysiloxanes such as dimethyl polysiloxane, methyl phenyl polysiloxane, and diphenyl polysiloxane are exemplified, and these dispersion media are preferably used. These dispersion media may be used singly or two or more dispersion media may be used in a mixture form.

In addition, as additional other dispersion media, cyclic polysiloxanes such as octamethyl cyclotetrasiloxane, decamethylcyclopentasiloxane, and dodecamethyl cyclohexasiloxane; and denatured polysiloxanes such as amino-denatured polysiloxane, polyether-denatured polysiloxane, alkyl-denatured polysiloxane, and fluorine-denatured polysiloxane are also preferably used. These dispersion media may be used singly or two or more dispersion media may be used in a mixture form.

In addition, as examples of other dispersion media that are different from the above-described other dispersion media, hydrophobic dispersion media such as hydrocarbon oils such as liquid paraffin, squalane, isoparaffin, branched chain-like light paraffin, petrolatum, and ceresin, ester oils such as isopropyl myristate, cetyl isooctanoate, and glyceryl trioctanoate, silicone oils such as decamethylcyclopentasiloxane, dimethyl polysiloxane, and methyl phenyl polysiloxane, higher fatty acids such as lauric acid, myristic acid, palmitic acid, and stearic acid, and higher alcohols such as lauryl alcohol, cetyl alcohol, stearyl alcohol, hexyl dodecanol, and isostearyl alcohol are also exemplified, only one dispersion medium may be used singly, or two or more dispersion media may be used in a mixture form.

The dispersion of the present embodiment may include an ordinarily-used additive as long as the characteristic thereof is not impaired. Examples of the additive include a dispersant, a stabilizer, a water-soluble binder, a viscosity improver, an oil-soluble preservative, an ultraviolet absorber, an oil-soluble chemical, an oil-soluble pigment, an oil-soluble protein, a plant oil, an animal oil, and the like. These additives may be contained in an arbitrarily selected amount.

The method for manufacturing the dispersion of the present embodiment is not particularly limited, and examples of the method include a method in which the zinc oxide powder of the present embodiment and a dispersion medium are mechanically dispersed using a well-known dispersion apparatus.

Examples of the dispersion apparatus include a stirrer, a planetary mixer, a homogenizer, an ultrasonic homogenizer, a sand mill, a ball mill, a roll mill, and the like.

The dispersion of the present embodiment can be preferably used for, in addition to cosmetics, paints and the like having an ultraviolet-shielding function, a gas transmission-suppressing function, or the like.

Paint

A paint of the present embodiment contains the zinc oxide powder of the present embodiment, a resin, and a dispersion medium.

The content of the zinc oxide powder in the paint of the present embodiment may be appropriately adjusted in accordance with a desired characteristic. The content of the zinc oxide powder is, for example, preferably 10% by mass or more and 40% by mass or less, more preferably 15% by mass or more and 35% by mass or less, and still more preferably 20% by mass or more and 30% by mass or less.

When the content of the zinc oxide powder in the paint is within the above-described range, the characteristic of the zinc oxide powder can be obtained, and it is possible to suppress a temporal increase in the viscosity of the paint.

The dispersion medium is not particularly limited as long as the dispersion medium is ordinarily used for industrial applications, and examples thereof include water, an alcohol such as methanol, ethanol, or propanol, and an organic solvent such as methyl acetate, ethyl acetate, toluene, methyl ethyl ketone, or methyl isobutyl ketone.

The content of the dispersion medium in the paint of the present embodiment is not particularly limited and is appropriately adjusted depending on the intended characteristic of the paint.

The resin can be used without any particular limitations as long as the resin is ordinarily used for industrial applications, and examples thereof include an acrylic resin, an epoxy resin, a urethane resin, a polyester resin, a silicone resin, and the like.

The content of the resin in the paint of the present embodiment is not particularly limited and is appropriately adjusted depending on the intended characteristic of the paint.

The paint of the present embodiment may include an ordinarily-used additive as long as the characteristic thereof is not impaired. Examples of the additives include a polymerization initiator, a dispersant, a preservative, and the like.

The method for manufacturing the paint of the present embodiment is not particularly limited, and examples of the method include a method in which the zinc oxide powder of the present embodiment, the resin, and the dispersion medium are mechanically mixed together using a well-known mixing apparatus. In addition, there is another method in which the above-described dispersion and the resin are mechanically mixed together using a well-known mixing apparatus.

Examples of the mixing apparatus include a stirrer, a planetary mixer, a homogenizer, an ultrasonic homogenizer, and the like.

A coated film can be formed by applying the paint of the present embodiment to a plastic base material such as a polyester film using an ordinary application method such as a roll coating method, a flow coating method, a spray coating method, a screen printing method, a brush coating method, or an immersion method. The coated film can be used as an ultraviolet-shielding film or a gas barrier film.

Cosmetic

A cosmetic of an embodiment of the present embodiment contains at least one selected from the group consisting of the zinc oxide powder of the present embodiment and the dispersion of the present embodiment. That is, the cosmetic may contain either or both of the zinc oxide powder and the dispersion. A cosmetic of another embodiment contains a base and at least one selected from the group consisting of the zinc oxide powder of the present embodiment and the dispersion of the present embodiment, which is to be dispersed in the base. That is, the cosmetic may contain either or both of the zinc oxide powder and the dispersion and the base material. The cosmetic of the present embodiment can be obtained by, for example, blending the dispersion of the present embodiment into a base such as an emulsion, a cream, a foundation, a lip stick, a blush, or an eye shadow as in the related art.

In addition, the cosmetic may also be obtained by blending the zinc oxide powder of the present embodiment into an oil phase or a water phase so as to produce an ON-type or W/O-type emulsion and then blending the emulsion with a base.

Hereinafter, a sunscreen cosmetic will be specifically described.

The content rate of the zinc oxide powder in the sunscreen cosmetic can be arbitrarily selected; however, in order to effectively shield ultraviolet rays, particularly, long-wavelength ultraviolet rays (UVA), the content rate of the zinc oxide powder is preferably 1% by mass or more and 30% by mass or less, more preferably 3% by mass or more and 20% by mass or less, and still more preferably 5% by mass or more and 15% by mass or less.

The sunscreen cosmetic may include a hydrophobic dispersion medium, inorganic fine particles or an inorganic pigment other than the zinc oxide powder, a hydrophilic dispersion medium, oil and fat, a surfactant, a moisturizing agent, a viscosity improver, a pH adjuster, a nutritional supplement, an antioxidant, a perfume, and the like as necessary.

Examples of the hydrophobic dispersion medium include a hydrocarbon oil such as such as liquid paraffin, squalane, isoparaffin, branched chain-like light paraffin, petrolatum, or ceresin, an ester oil such as isopropyl myristate, cetyl isooctanoate, or glyceryl trioctanoate, a silicone oil such as decamethylcyclopentasiloxane, dimethyl polysiloxane, or methyl phenyl polysiloxane, a higher fatty acid such as lauric acid, myristic acid, palmitic acid, or stearic acid, and a higher alcohol such as lauryl alcohol, cetyl alcohol, stearyl alcohol, hexyl dodecanol, or isostearyl alcohol.

Examples of the inorganic fine particles or the inorganic pigment other than the zinc oxide powder include calcium carbonate, calcium phosphate (apatite), magnesium carbonate, calcium silicate, magnesium silicate, aluminum silicate, kaolin, talc, titanium oxide, aluminum oxide, yellow oxide of iron, γ-iron oxide, cobalt titanate, cobalt violet, silicon oxide, and the like.

The sunscreen cosmetic may further contain at least one organic ultraviolet absorber. The content of the organic ultraviolet absorber may be appropriately adjusted so as to obtain a desired ultraviolet-shielding property. For the organic ultraviolet absorber the amount of which that can be blended into sunscreen cosmetic is regulated, the upper limit may be appropriately adjusted according to the regulation of each country. For example, the content of the organic ultraviolet absorber may be 20% by mass or less, 15% by mass, 12% by mass or less, or 10% by mass or less, 9% by mass or less, 8% by mass or less, 6% by mass or less, 4% by mass or less, or 3% by mass or less.

Examples of the organic ultraviolet absorber include a benzotriazole-based ultraviolet absorber, a benzoyl methane-based ultraviolet absorber, a benzoic acid-based ultraviolet absorber, an anthranilic acid-based ultraviolet absorber, a salicylic acid-based ultraviolet absorber, a cinnamic acid-based ultraviolet absorber, a silicone-based ultraviolet absorber, a triazine-based ultraviolet absorber, an imidazole-based ultraviolet absorber, a camphor-based ultraviolet absorber, a benzophenone-based ultraviolet absorber, organic ultraviolet absorbers other than the above-described ultraviolet absorbers, and the like.

Examples of an example of the benzotriazole-based ultraviolet absorber include 2-(2'-hydroxy-5'-t-octylphenyl)benzotriazole, 2-(2'-hydroxy-5'-methylphenyl) benzotriazole, and the like.

Examples of an example of the benzoyl methane-based ultraviolet absorber include dibenzalazine, dianisoylmethane, 4-tert-butyl-4'-methoxydibenzoylmethane, 1-(4'-isopropylphenyl)-3-phenyl propane-1,3-dione, 5-(3,3'-dimethyl-2-norbornylidene)-3-pentane-2-one, and the like.

Examples of an example of the benzoic acid-based ultraviolet absorber include para-aminobenzoic acid (PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA methyl ester, ethylhexyl dimethyl PABA, amyl dimethyl PABA, and the like.

Examples of an example of the anthranilic acid-based ultraviolet absorber include homo menthyl-N-acetyl anthranilate and the like.

Examples of an example of the salicylic acid-based ultraviolet absorber include amyl salicylate, menthyl salicylate, homo menthyl salicylate, octyl salicylate, phenyl salicylate, benzyl salicylate, p-2-propnol phenyl salicylate, ethylhexyl salicylate, and the like.

Examples of an example of the cinnamic acid-based ultraviolet absorber include octyl methoxycinnamate, di-para methoxy cinnamate-mono-2-glyceryl ethylhexanoate, octyl cinnamate, ethyl-4-isopropyl cinnamate, diisoprpyle methyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate(2-ethylhexyl-p-methoxy cinnmate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethylhexanoyl-diparamethoxy cinnamate, ferulic acid, cinoxate, isophenyl trimethoxycinnamate trisiloxane, isopropyl methoxycinnamate, and the like.

Examples of an example of the silicone-based ultraviolet absorber include [3-bis(trimethylsiloxy)methylsilyl-1-methylpropyl]-3,4,5-trimethoxy cinnamate, [3-bis(trimethylsiloxy)methylsilyl-3-methylpropyl]-3,4,5-trimethoxy cinnamate, [3-bis(trimethylsiloxy)methylsilylpropyl]-3,4,5-trimethoxy cinnamate, [3-bis(trimethylsiloxy) methylsilylbutyl]-3,4,5-trimethoxy cinnamate, [3-tris(trimethylsiloxy)silylbutyl]-3,4,5-trimethoxy cinnamate, [3-tris(trimethylsiloxy)silyl-1-methylpropyl]-3,4-dimethoxy cinnamate, polysilicone-15, drometrizole trisiloxane, and the like.

Examples of an example of the triazine-based ultraviolet absorber include bis-ethylhexyloxyphenol methoxyphenyl triazine, ethylhexyl triazone, methylene bis-benzotriazolyl tetramethylbutylphenol, tris-biphenyl triazine, diethylhexyl butamido triazone, and the like.

Examples of an example of the imidazole-based ultraviolet absorber include disodium phenyl dibenzimidazole tetrasulfonate, phenylbenzimidazole sulfonic acid, ethylhexyl dimethoxybenzylidene dioxoimidazolidine propionate, and the like.

Examples of an example of the camphor-based ultraviolet absorber include 3-(4'-methylbenzylidene)-d,l-camphor, 3-benzylidene-d,l-camphor, terephthalylidene dicamphor sulfonic acid, camphor benzalkonium methsulfate, benzylidene camphor sulfonic acid, polyacrylamidomethyl benzylidene camphor, and the like.

Examples of an example of the benzophenone-based ultraviolet absorber include oxybenzone-1, oxybenzone-2, oxybenzone-3, oxybenzone-4, oxybenzone-5, oxybenzone-6, oxybenzone-7, oxybenzone-8, oxybenzone-9,4-(2-β-glucopyranosiloxy)propoxy-2-hydroxybenzophenone, and the like.

Examples of the organic ultraviolet absorbers other than the above-described ultraviolet absorbers include urocanic acid, ethyl urocanate ester, 5-methyl-2-phenylbenzoxazole, 5-(3,3'-dimethyl-2-norbornylidene)-3-pentane-2-one, diethylamino hydroxybenzoyl hexyl benzoate, octocrylene, a silicone-denatured ultraviolet absorber, a fluorine-denatured ultraviolet absorber, and the like.

As described above, according to the zinc oxide powder of the present embodiment, the BET specific surface area, the apparent specific volume measured by the loose packing method, and the ratio of the apparent specific volume measured by the loose packing method/the apparent specific volume measured by the tapping method are adjusted to predetermined ranges. Therefore, it is possible to suppress a temporal increase in the viscosity of dispersions or the like containing this zinc oxide powder. In addition, the use of this zinc oxide powder makes it possible to obtain dispersions or cosmetics having high transparency and an excellent ultraviolet-shielding property. The above-described characteristic is an extremely excellent effect.

According to the surface-treated zinc oxide powder of the present embodiment, the surface treatment is performed on at least some of the surface of the zinc oxide powder of the present embodiment with at least one of the inorganic component and the organic component. Therefore, it is possible to suppress the surface activity of the zinc oxide powder and to improve the dispersibility in dispersion media. Therefore, it is possible to suppress a temporal increase in the viscosity of dispersions or the like containing this surface-treated zinc oxide powder. In addition, it is possible to obtain an effect of high transparency as in the related art.

The dispersion of the present embodiment contains the zinc oxide powder or surface-treated zinc oxide powder of the present embodiment. Therefore, it is possible to suppress a temporal increase in the viscosity of the dispersion.

The paint of the present embodiment contains the zinc oxide powder or surface-treated zinc oxide powder of the present embodiment. Therefore, it is possible to suppress a temporal increase in the viscosity of the paint.

The cosmetic of the present embodiment contains the zinc oxide powder or surface-treated zinc oxide powder of the present embodiment. Therefore, it is possible to suppress a temporal increase in the viscosity of the cosmetic.

EXAMPLES

Hereinafter, the present invention will be more specifically described with examples and comparative examples, but the present invention is not limited to the following examples.

Method for Manufacturing Zinc Oxide Powder

Example 1

Production of Surface-Treated Zinc Oxide Powder

A zinc oxide powder A1 (BET specific surface area: 39.6 $m^2/g$, apparent specific volume measured by loose packing method: 7.31 mL/g, apparent specific volume measured by tapping method: 3.85 mL/g, crystallite diameter: 17 nm, and oil absorption amount: 140 mL/100 g) was prepared. The above-described characteristic, crystallite diameter, BET-converted particle diameter, and crystallite diameter (nm)/BET-converted diameter (nm) of the zinc oxide powder A1 are shown in Table 1.

A mixed liquid containing octyltriethoxysilane (trade name: KBE-3083, manufactured by Shin-Etsu Chemical Co., Ltd.) (6 parts by mass), the zinc oxide powder A1 (100 parts by mass), pure water (0.6 parts by mass), and isopropyl alcohol (34.1 parts by mass) was mixed in a Henschel mixer.

Next, the mixed liquid was dried at 80° C. until the isopropyl alcohol was removed. Next, the obtained dried substance was cracked by 16000 rotations in a hammer mill until D98 became 500 μm or less. This cracked powder was dried at 120° C. for three hours, thereby obtaining a surface-treated zinc oxide powder B1 of Example 1. D98 (μm) of the surface-treated zinc oxide powder B1 is shown in Table 1. Regarding D98, the volume particle size distribution of the zinc oxide powder B1 was measured using a laser diffraction-type particle size distribution-measuring device (Model No.: Mastersizer 3000, manufactured by Malvern Panalytical Ltd.), and the value of the particle diameter at a cumulative volume percentage of 98% was obtained as D98.

Production of Dispersion

The surface-treated zinc oxide powder B1 of Example 1 (50 parts by mass), PEG-9 polydimethylsiloxyethyl dimethicone (trade name: KF-6028, manufactured by Shin-Etsu Chemical Co., Ltd.) (10 parts by mass), and decamethylcyclopentasiloxane (trade name: SH245Fluid, manufactured by Dow Toray Co., Ltd.) (40 parts by mass) were mixed and dispersed using a bead mill, thereby obtaining a dispersion C1 of Example 1.

Evaluation of Viscosity and Temporal Stability of Dispersion

The viscosity of the dispersion C1 of Example 1 was measured under the following conditions using a rheometer (trade name: Modular Compact Rheometer MCR 102, manufactured by Anton Paar GmbH). The results are shown in Table 1.

Measurement temperature: 25° C.
Jig: Cone plate CP25-2
Shear rate: 1/sec

This dispersion was stored at 50° C. for 28 days, and the viscosity was measured under the same conditions as described above. The results are shown in Table 1.

Evaluation of Transparency and Ultraviolet-Shielding Property

The dispersion of Example 1 was diluted with decamethylcyclopentasiloxane such that the content of the surface-treated zinc oxide powder became 0.005% by mass. The linear transmittances of this diluted solution at 308 nm and 555 nm were measured using an UV-visible/NIR spectrophotometer (manufactured by JASCO Corporation, Model No.: V-770). The results are shown in Table 1.

A low transmittance at 308 nm indicates that the ultraviolet-shielding property is favorable. Therefore, the linear transmittance at 308 nm is preferably low.

A high transmittance at 555 nm indicates that the transparency is favorable. Therefore, the transmittance at 555 nm is preferably high.

Example 2

A surface-treated zinc oxide powder B2 of Example 2 and a dispersion C2 containing the surface-treated zinc oxide powder B2 were obtained in completely the same manner as in Example 1 except that, instead of the zinc oxide powder A1, a zinc oxide powder A2 (BET specific surface area: 40.4 $m^2/g$, apparent specific volume measured by loose packing method: 6.43 mL/g, apparent specific volume measured by the tapping method: 3.81 mL/g, crystallite diameter: 17 nm, and oil absorption amount: 126 mL/100 g) was used.

The results of the same evaluations as in Example 1 are shown in Table 1.

Example 3

A surface-treated zinc oxide powder B3 of Example 3 and a dispersion C3 containing the surface-treated zinc oxide powder B3 were obtained in completely the same manner as in Example 1 except that, instead of the zinc oxide powder A1, a zinc oxide powder A3 (BET specific surface area: 39.8 $m^2/g$, apparent specific volume measured by loose packing method: 5.21 mL/g, apparent specific volume measured by the tapping method: 2.90 mL/g, crystallite diameter: 16 nm, and oil absorption amount: 116 mL/100 g) was used.

The results of the same evaluations as in Example 1 are shown in Table 1.

Example 4

A surface-treated zinc oxide powder B4 of Example 4 and a dispersion C4 containing the surface-treated zinc oxide powder B4 were obtained in completely the same manner as in Example 1 except that, instead of the zinc oxide powder A1, a zinc oxide powder A4 (BET specific surface area: 34.1 m$^2$/g, apparent specific volume measured by loose packing method: 1.60 mL/g, apparent specific volume measured by the tapping method: 1.05 mL/g, crystallite diameter: 15 nm, and oil absorption amount: 94 mL/100 g) was used.

The results of the same evaluations as in Example 1 are shown in Table 1.

Example 5

A surface-treated zinc oxide powder B5 of Example 5 and a dispersion C5 containing the surface-treated zinc oxide powder B5 were obtained in completely the same manner as in Example 1 except that, instead of the zinc oxide powder A1, a zinc oxide powder A5 (BET specific surface area: 10.5 m$^2$/g, apparent specific volume measured by loose packing method: 1.64 mL/g, apparent specific volume measured by the tapping method: 1.07 mL/g, crystallite diameter: 25 nm, and oil absorption amount: 92 mL/100 g) was used.

The results of the same evaluations as in Example 1 are shown in Table 1.

Example 6

A surface-treated zinc oxide powder B6 of Example 6 and a dispersion C6 containing the surface-treated zinc oxide powder B6 were obtained in completely the same manner as in Example 1 except that, instead of the zinc oxide powder A1, a zinc oxide powder A6 (BET specific surface area: 37.2 m$^2$/g, apparent specific volume measured by loose packing method: 3.30 mL/g, apparent specific volume measured by the tapping method: 1.95 mL/g, crystallite diameter: 16 nm, and oil absorption amount: 108 mL/100 g) was used.

The results of the same evaluations as in Example 1 are shown in Table 1.

Example 7

A surface-treated zinc oxide powder B7 of Example 7 and a dispersion C7 containing the surface-treated zinc oxide powder B7 were obtained in completely the same manner as in Example 1 except that, instead of the zinc oxide powder A1, a zinc oxide powder A7 (BET specific surface area: 34.6 m$^2$/g, apparent specific volume measured by loose packing method: 6.36 mL/g, apparent specific volume measured by the tapping method: 2.93 mL/g, crystallite diameter: 18 nm, and oil absorption amount: 93 mL/100 g) was used.

The results of the same evaluations as in Example 1 are shown in Table 1.

Example 8

A surface-treated zinc oxide powder B8 of Example 8 and a dispersion C8 containing the surface-treated zinc oxide powder B8 were obtained in completely the same manner as in Example 1 except that, instead of the zinc oxide powder A1, a zinc oxide powder A8 (BET specific surface area: 52.5 m$^2$/g, apparent specific volume measured by loose packing method: 1.80 mL/g, apparent specific volume measured by the tapping method: 1.15 mL/g, crystallite diameter: 15 nm, and oil absorption amount: 105 mL/100 g) was used.

The results of the same evaluations as in Example 1 are shown in Table 1.

In all of the zinc oxide powders A1 to A8 used in the examples, the value obtained by dividing the dry particle diameter D98 (μm) by the BET-converted particle diameter (nm) was 0.01 or more and 5 or less.

Comparative Example 1

A surface-treated zinc oxide powder B9 of Comparative Example 1 and a dispersion C9 containing the surface-treated zinc oxide powder B9 were obtained in completely the same manner as in Example 1 except that, instead of the zinc oxide powder A1, a zinc oxide powder A9 that was a commercially available product (BET specific surface area: 44.8 m$^2$/g, apparent specific volume measured by loose packing method: 7.99 mL/g, apparent specific volume measured by the tapping method: 4.92 mL/g, crystallite diameter: 14 nm, and oil absorption amount: 163 mL/100 g) was used.

The results of the same evaluations as in Example 1 are shown in Table 1.

Comparative Example 2

A surface-treated zinc oxide powder B10 of Comparative Example 2 and a dispersion C10 containing the surface-treated zinc oxide powder B10 were obtained in completely the same manner as in Example 1 except that, instead of the zinc oxide powder A1, a zinc oxide powder A10 that was a commercially available product (BET specific surface area: 36.8 m$^2$/g, apparent specific volume measured by loose packing method: 5.49 mL/g, apparent specific volume measured by the tapping method: 3.73 mL/g, crystallite diameter: 18 nm, and oil absorption amount: 104 mL/100 g) was used.

The results of the same evaluations as in Example 1 are shown in Table 1.

Comparative Example 3

A surface-treated zinc oxide powder B11 of Comparative Example 3 and a dispersion C11 containing the surface-treated zinc oxide powder B11 were obtained in completely the same manner as in Example 1 except that, instead of the zinc oxide powder A1, a zinc oxide powder A11 (BET specific surface area: 55.2 m$^2$/g, apparent specific volume measured by loose packing method: 8.18 mL/g, apparent specific volume measured by the tapping method: 3.15 mL/g, crystallite diameter: 16 nm, and oil absorption amount: 154 mL/100 g) was used.

The results of the same evaluations as in Example 1 are shown in Table 1.

Comparative Example 4

A surface-treated zinc oxide powder B12 of Comparative Example 4 and a dispersion C12 containing the surface-treated zinc oxide powder B12 were obtained in completely the same manner as in Example 1 except that, instead of the zinc oxide powder A1, a zinc oxide powder A12 (BET specific surface area: 35.5 m$^2$/g, apparent specific volume measured by loose packing method: 6.15 mL/g, apparent specific volume measured by the tapping method: 4.45 mL/g, crystallite diameter: 18 nm, and oil absorption amount: 95 mL/100 g) was used.

The results of the same evaluations as in Example 1 are shown in Table 1.

TABLE 1

| | | Example 1 | Example 2 | Example 3 | Example 4 | Example 5 | Example 6 | Example 7 | Example 8 |
|---|---|---|---|---|---|---|---|---|---|
| Zinc oxide powder | BET specific surface area (m²/g) | 39.6 | 40.4 | 39.8 | 34.1 | 10.5 | 37.2 | 34.6 | 52.5 |
| | BET-converted diameter (nm) | 27.0 | 26.5 | 26.9 | 31.4 | 101.9 | 28.8 | 30.9 | 20.4 |
| | Loosely packed volume (mL/g) | 7.31 | 6.43 | 5.21 | 1.60 | 1.64 | 3.30 | 6.36 | 1.80 |
| | Tapped volume (mL/g) | 3.85 | 3.81 | 2.90 | 1.05 | 1.07 | 1.95 | 2.93 | 1.15 |
| | Loosely packed volume/tapped volume | 1.90 | 1.69 | 1.80 | 1.52 | 1.53 | 1.69 | 2.17 | 1.57 |
| | Oil absorption amount (mL/100 g) (linseed oil) | 140 | 126 | 116 | 94 | 92 | 108 | 93 | 105 |
| | Crystallite diameter (nm) | 17 | 17 | 16 | 15 | 25 | 16 | 18 | 15 |
| | Crystallite diameter (nm)/BET-converted diameter (nm) | 0.63 | 0.64 | 0.59 | 0.48 | 0.25 | 0.56 | 0.58 | 0.74 |
| Surface-treated zinc oxide powder | Dry particle diameter (μm) | 5.8 | 8.0 | 10.8 | 12.0 | 420.0 | 10.2 | 15.0 | 7.2 |
| | Dry particle diameter (μm)/BET-converted diameter (nm) | 0.21 | 0.30 | 0.40 | 0.38 | 4.12 | 0.35 | 0.48 | 0.35 |
| Disperson | Initial viscosity (mPa · s) | 300 | 180 | 90 | 50 | 30 | 60 | 60 | 80 |
| | Viscosity after 28 days at 50° C. (mPa · s) | 440 | 260 | 160 | 80 | 50 | 120 | 100 | 150 |
| | Transmittance at 308 nm (%) | 28 | 30 | 33 | 27 | 42 | 30 | 32 | 36 |
| | Transmittance at 555 nm (%) | 92 | 91 | 88 | 92 | 75 | 90 | 90 | 94 |

| | | Comparative Example 1 | Comparative Example 2 | Comparative Example 3 | Comparative Example 4 |
|---|---|---|---|---|---|
| Zinc oxide powder | BET specific surface area (m²/g) | 44.8 | 36.8 | 55.2 | 35.5 |
| | BET-converted diameter (nm) | 23.9 | 29.1 | 19.4 | 30.1 |
| | Loosely packed volume (mL/g) | 7.99 | 5.49 | 8.18 | 6.15 |
| | Tapped volume (mL/g) | 4.92 | 3.73 | 3.15 | 4.45 |
| | Loosely packed volume/tapped volume | 1.62 | 1.47 | 2.60 | 1.38 |
| | Oil absorption amount (mL/100 g) (linseed oil) | 163 | 104 | 154 | 95 |
| | Crystallite diameter (nm) | 14 | 18 | 16 | 18 |
| | Crystallite diameter (nm)/BET-converted diameter (nm) | 0.59 | 0.62 | 0.83 | 0.60 |
| Surface-treated zinc oxide powder | Dry particle diameter (μm) | 22.5 | 44.9 | 14.5 | 9.5 |
| | Dry particle diameter (μm)/BET-converted diameter (nm) | 0.94 | 1.54 | 0.75 | 0.32 |

TABLE 1-continued

| Disperson | Initial viscosity (mPa·s) | Gelatinized | 90 | 1200 | 210 |
|---|---|---|---|---|---|
| | Viscosity after 28 days at 50° C. (mPa·s) | Unmeasurable | 12600 | Gelatinized | 10400 |
| | Transmittance at 308 nm (%) | — | 28 | 31 | 32 |
| | Transmittance at 555 nm (%) | — | 91 | 91 | 90 |

In Table 1, the loosely packed volume represents the apparent specific volume measured by the loose packing method. The tapped volume represents the apparent specific volume measured by tapping method.

It was confirmed from the comparison between Example 1 to Example 8 and Comparative Example 1 to Comparative Example 4 that, in the dispersions containing zinc oxide particles having a BET specific surface area of 8 m$^2$/g or more and 65 m$^2$/g or less, an apparent specific volume measured by the loose packing method of 1.0 mL/g or more and 7.5 mL/g or less, and an apparent specific volume measured by loose packing method/apparent specific volume measured by tapping method of 1.50 or more and 2.50 or less, a temporal increase in the viscosity was suppressed while maintaining the oil absorption amount within the preferable range. In addition, it was also confirmed that the same degree of transparency and ultraviolet-shielding property as in the related art were obtained. These are extremely excellent effects that could not be obtained in the related art.

In addition, compared with the surface-treated zinc oxide powders of Example 1 to Example 4 and Example 6 to Example 8, in the surface-treated zinc oxide powder B5 of Example 5, the texture of rough surface was strong when the surface-treated zinc oxide powder was touched with a finger. That is, it was confirmed that, in the surface-treated zinc oxide powder having a D98/BET-converted particle diameter of 0.01 or more and 3.0 or less, the texture of rough surface was suppressed. In the present invention, it was possible to obtain an excellent effect of maintaining the oil absorption amount while preventing an increase in the viscosity of the zinc oxide powder, which has not been solved in the related art.

INDUSTRIAL APPLICABILITY

The zinc oxide powder of the present invention is capable of suppressing a temporal increase in the viscosity in the case of being dispersed in a dispersion medium to produce a dispersion. Therefore, the zinc oxide powder of the present invention is excellent in terms of stability in the case of being applied to dispersions, paints, and cosmetics and has a significant industrial value.

The present invention is capable of providing a zinc oxide powder having a high oil absorption amount and capable of suppressing a temporal increase in the case of being blended into dispersions or the like and a dispersion, a paint, and a cosmetic that each contain the zinc oxide powder.

What is claimed is:

1. A zinc oxide powder,
   wherein a BET specific surface area of the powder is 8 m$^2$/g or more and 65 m$^2$/g or less,
   an apparent specific volume measured by a loose packing method of the powder is 1.0 mL/g or more and 7.5 mL/g or less, and
   a value indicated by (the apparent specific volume measured by the loose packing method/an apparent specific volume measured by a tapping method), which is obtained by dividing the apparent specific volume (mL/g) measured by the loose packing method by the apparent specific volume (mL/g) measured by the tapping method of the powder, is 1.50 or more and 2.50 or less.

2. The zinc oxide powder according to claim 1,
   wherein a value obtained by dividing a dry particle diameter D98 (μm) of the powder by a BET-converted particle diameter (nm) of the powder is 0.01 or more and 5.0 or less.

3. The zinc oxide powder according to claim 1,
   wherein a BET-converted particle diameter of the zinc oxide powder is 10 to 110 nm.

4. The zinc oxide powder according to claim 3,
   wherein a value obtained by a formula: a crystallite diameter (nm) of the zinc oxide powder/the BET-converted particle diameter (nm) of the zinc oxide powder is 0.1 or more and 1.0 or less.

5. The zinc oxide powder according to claim 4,
   wherein an oil absorption amount of the zinc oxide powder is 80 to 150 mL/100 g.

6. The zinc oxide powder according to claim 1,
   wherein the zinc oxide powder consists of zinc oxide particles.

7. The zinc oxide powder according to claim 1,
   wherein the zinc oxide powder is a surface-treated powder which is surface-treated with at least one of an inorganic component and an organic component.

8. The zinc oxide powder according to claim 7,
   wherein a value obtained by dividing a dry particle diameter D98 (μm) of the powder by a BET-converted particle diameter (nm) of the powder is 0.01 or more and 5 or less.

9. The zinc oxide powder according to claim 8,
   wherein the value obtained by dividing the dry particle diameter D98 (μm) of the powder by the BET-converted particle diameter (nm) of the powder is 0.01 or more and 3.0 or less.

10. The zinc oxide powder according to claim 1,
    wherein the apparent specific volume (mL/g) measured by the loose packing method is a value which is measured in accordance with JIS K5101-12-1, and
    the apparent specific volume (mL/g) measured by the tapping method is a value measured by
    passing a zinc oxide powder through a sieve having a mesh diameter of 500 μm,
    adding the zinc oxide powder which has been passed through the sieve to a 150 mL graduated cylinder, wherein the weight of the cylinder is known, until the volume of the powder becomes 100 mL,
    measuring the weight of the graduated cylinder which includes the powder, covering the measured graduated cylinder with a lid,
fixing the covered graduated cylinder to a bulk density-measuring device, and performing tapping thereon 50 times,
reading the volume of the zinc oxide powder after tapping, and
obtaining a value as the apparent specific volume by dividing the volume of the zinc oxide powder after tapping by the weight of the zinc oxide powder in the graduated cylinder.

11. A dispersion comprising:
the zinc oxide powder according to claim 1; and
a dispersion medium.

12. A paint comprising:
the zinc oxide powder according to claim 1;
a resin; and
a dispersion medium.

13. A cosmetic comprising:
the zinc oxide powder according to claim 1.

14. A cosmetic comprising:
the zinc oxide powder according to claim 1; and
a dispersion medium.

* * * * *